United States Patent
Zhu et al.

(10) Patent No.: US 6,810,287 B2
(45) Date of Patent: Oct. 26, 2004

(54) IMPLANTABLE CARDIAC DISEASE MANAGEMENT DEVICE WITH TRIGGER-STORED POLYSOMNOGRAM AND PHONOCARDIOGRAM

(75) Inventors: Qingsheng Zhu, Little Canada, MN (US); Jeffrey E. Stahmann, Ramsey, MN (US); John Hatlestad, Burnsville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 424 days.

(21) Appl. No.: 10/006,183

(22) Filed: Dec. 3, 2001

(65) Prior Publication Data
US 2003/0105497 A1 Jun. 5, 2003

(51) Int. Cl.[7] .............................................. A61N 1/365
(52) U.S. Cl. ........................................................ 607/17
(58) Field of Search ................................ 607/6, 17–25; 600/513, 528, 547

(56) References Cited

U.S. PATENT DOCUMENTS 5,876,353 A * 3/1999 Riff .............................. 600/547
5,935,081 A * 8/1999 Kadhiresan ................ 600/513

* cited by examiner

Primary Examiner—George Manuel
(74) Attorney, Agent, or Firm—Thomas J. Nikolai; Nikolai & Mersereau, P.A.

(57) ABSTRACT

Currently, brady, tachy and CRT devices all provide stored electrograms that record ambulatory electrograms with programmable trigger mechanisms. The present invention comprises an implantable device with additional capability that can store polysomnograms and phonocardiograms. The polysomnograms can be obtained from an impendent sensor of the type used in minute ventilation-based rate-adaptive pacemakers. The phonocardiograms are obtained from an accelerometer transducer or other type sensors that can detect heart sound.

6 Claims, 8 Drawing Sheets

IMPLANTABLE CARDIAC DISEASE MANAGEMENT DEVICE WITH TRIGGER-STORED POLYSOMNOGRAM AND PHONOCARDIOGRAM

BACKGROUND OF THE INVENTION

1. Field of the Invention

This invention relates generally to body-implantable, medical apparatus, and more particularly to a cardiac rhythm management device (CRMD) having a capability of recording polysomnogram (PSG) data and/or phonocardiogram (heart sound) data upon the detection of pre-programmed conditions or events.

2. Discussion of the Prior Art

State of the art implantable medical devices, such as pacemakers and defibrillators, typically embody a microprocessorbased controller capable of receiving as inputs, digitized signals corresponding to heart depolarization events and other sensor derived outputs and for controlling a pulse generator that generates tissue-stimulating pulses in accordance with a program stored in a memory for the microprocessor-based controller. Such devices also typically include a telemetry link whereby programmed data and operands can be exchanged between the implanted device and an external programmer/monitor.

The memory in the implant may also be used to record, when enabled, electrogram signals for later read-out and analysis by a medical professional.

It is also known that cardiac pacing can be used as a therapy for patients with congestive heart failure (CHF). Algorithms have been developed for establishing a AV-delay interval that optimizes the pumping performance of the sick heart.

In applying cardiac pacing as a treatment for CHF, not only is electrogram data derived from an implanted CRMD of interest, but other physiologic sensor derived data may also prove helpful in treating the patient. For example, heart sound data can prove meaningful.

As is well known, the first heart sound, $S_1$, is initiated at the onset of ventricular systole and consists of a series of vibrations of mixed, unrelated, low frequencies. It is the loudest and longest of the heart sounds, has a decrescendo quality, and is heard best over the apical region of the heart. The tricuspid valve sounds are heard best in the fifth intercostal space, just to the left of the sternum, and the mitral sounds are heard best in the fifth intercostal space at the cardiac apex.

$S_1$ is chiefly caused by oscillation of blood in the ventricular chambers and vibration of the chamber walls. The vibrations are engendered by the abrupt rise of ventricular pressure with acceleration of blood back toward the atria, and the sudden tension and recoil of the A-V valves and adjacent structures with deceleration of the blood by the closed A-V valves. The vibrations of the ventricles and the contained blood are transmitted through surrounding tissue and reach the chest wall where they may be heard or recorded.

In accordance with the present invention, an implanted CRMD may include an accelerometer as a sound transducer and because implanted in close proximity to the heart, may develop a robust electrical signal that can be digitized and stored in the memory of the implant.

The intensity of the first sound is primarily a function of the force of the ventricular contraction, but also of the interval between atrial and ventricular systoles. If the A-V valve leaflets are not closed prior to ventricular systole, greater velocity is imparted to the blood moving toward the atria by the time the A-V valves are snapped shut by the rising ventricular pressure, and stronger vibrations result from this abrupt deceleration of the blood by the closed A-V valves.

The second heart sound, $S_2$, which occurs on closure of the semi-lunar valves, is composed of higher frequency vibrations, is of shorter duration and lower intensity, and has a more "snapping" quality than the first heart sound. The second sound is caused by abrupt closure of the semi-lunar valves, which initiates oscillations of the columns of blood and the tensed vessel walls by the stretch and recoil of the closed valve. Conditions that bring about a more rapid closure of the semi-lunar valve, such as increases in pulmonary artery or aorta pressure (e.g., pulmonary or systemic hypertension), will increase the intensity of the second heart sound. In the adult, the aortic valve sound is usually louder than the pulmonic, but in cases of pulmonary hypertension, the reverse is often true.

The third heart sound, which is more frequently heard in children with thin chest walls or in patients with left ventricular failure due to CHF, consists of a few low intensity, low-frequency vibrations. It occurs in early diastole and is believed to be due to vibrations of the ventricular walls caused by abrupt acceleration and deceleration of blood entering the ventricles on opening of the atrial ventricular valves.

A fourth or atrial sound, $(S_4)$, consisting of a few low-frequency oscillations, is occasionally heard in normal individuals. It is caused by oscillation of blood and cardiac chambers created by atrial contraction.

When $S_3$ and $S_4$ sounds are accentuated, it may be indicative of certain abnormal conditions and are of diagnostic significance. Therefore, the ability to store heart sound information for later playback can prove beneficial to medical professionals following patients in whom cardiac pacemakers and/or defibrillators are implanted.

In addition to heart sound information, benefit can also be derived from the storage and later read out from an implanted CRMD of respiratory related data. While external polysomnograph equipment can be worn for recording respiratory related data over extended time intervals, the ability to derive polysomnograms from an implanted CRMD can prove to be beneficial. Such things as Cheyne-Stokes respiration patterns, Biot's respiration, Epnustic breathing and central neurogenic hypoventilation and hyperventilation can be detected and recorded.

In Cheyne-Stokes respiration, respiratory rate and tidal volume gradually increase, then gradually decrease to complete apnea, which may last several seconds. Then, tidal volume and breathing frequency gradually increases again, repeating the cycle. This pattern occurs when cardiac output is low, as in CHF, delaying the blood transit time between the lungs and the brain. In this instance, changes in respiratory center $Pco_2$ lag changes in arterial $Pco_2$. For example, when an increased $Paco_2$ from the lungs reaches the respiratory neurons, ventilation is stimulated, which then lowers the atrial $Pco_2$ level. By the time this reduced $Paco_2$ reaches the medulla to inhibit ventilation, hyperventilation has been in progress for an inappropriately long time. When blood from the lung finally does reach the medullary centers, the low $Paco_2$ greatly depresses ventilation to the point of apnea. Atrial $Pco_2$ then rises, but a rise in respiratory center $Pco_2$ is delayed because of low blood flow rate. The brain eventually does receive the high Paco$_2$ signal, and the cycle is repeated. Cheyne-Stokes respiration also may be caused by brain injuries, in which respiratory centers correspond to changes Pco$_2$ level are damaged.

It is accordingly a principal object of the present invention to provide an implantable CRMD capable of producing and storing in a memory phonocardiograms of heart sounds and polysomnograms reflecting respiratory events for later readout from the device via a conventional telemetry link used in such devices.

It is still another object of the present invention to establish certain triggering mechanisms for enabling the memory to capture certain respiratory patterns such as those related to Cheyne-Stokes patterns by monitoring tidal volume or respiratory rate variations with respect to a predetermined threshold. Similarly, the system may be enabled to capture heart sound information when, for example, atrial fibrillation occurs or, perhaps, at a certain level of exercise.

SUMMARY OF THE INVENTION

The foregoing objects are achieved in accordance with the present invention by providing an implantable cardiac rhythm management device of a type having a microprocessor-based controller along with a memory. The CRMD may also comprise a pulse generator for producing cardiac stimulating pulses at times determined by the program run on the microprocessor-based controller. Alternatively, the implant may be a purely diagnostic device. The CRMD also incorporates a means for sensing at least one of respiratory related activity and heart sounds. A triggering device is incorporated that is responsive to a predetermined event for initiating storage of data pertaining to the sensed one of respiratory related activity and heart sounds in the memory. As an example, upon detection of a predetermined respiratory pattern, the memory may be enabled for storing polysomnogram data. Alternatively, the occurrence of an event, such as an onset of atrial fibrillation, may be used to trigger the memory so as to store phonocardiogram data. The recording function in the memory of the implanted device can also be manually triggered, using an external magnet.

DESCRIPTION OF THE DRAWINGS

The foregoing features, objects and advantages of the invention will become apparent to those skilled in the art from the following detailed description of a preferred embodiment, especially when considered in conjunction with accompanying drawings in which like numerals in the several views refer to corresponding parts.

DESCRIPTION OF THE PREFERRED EMBODIMENT

Figure 1:
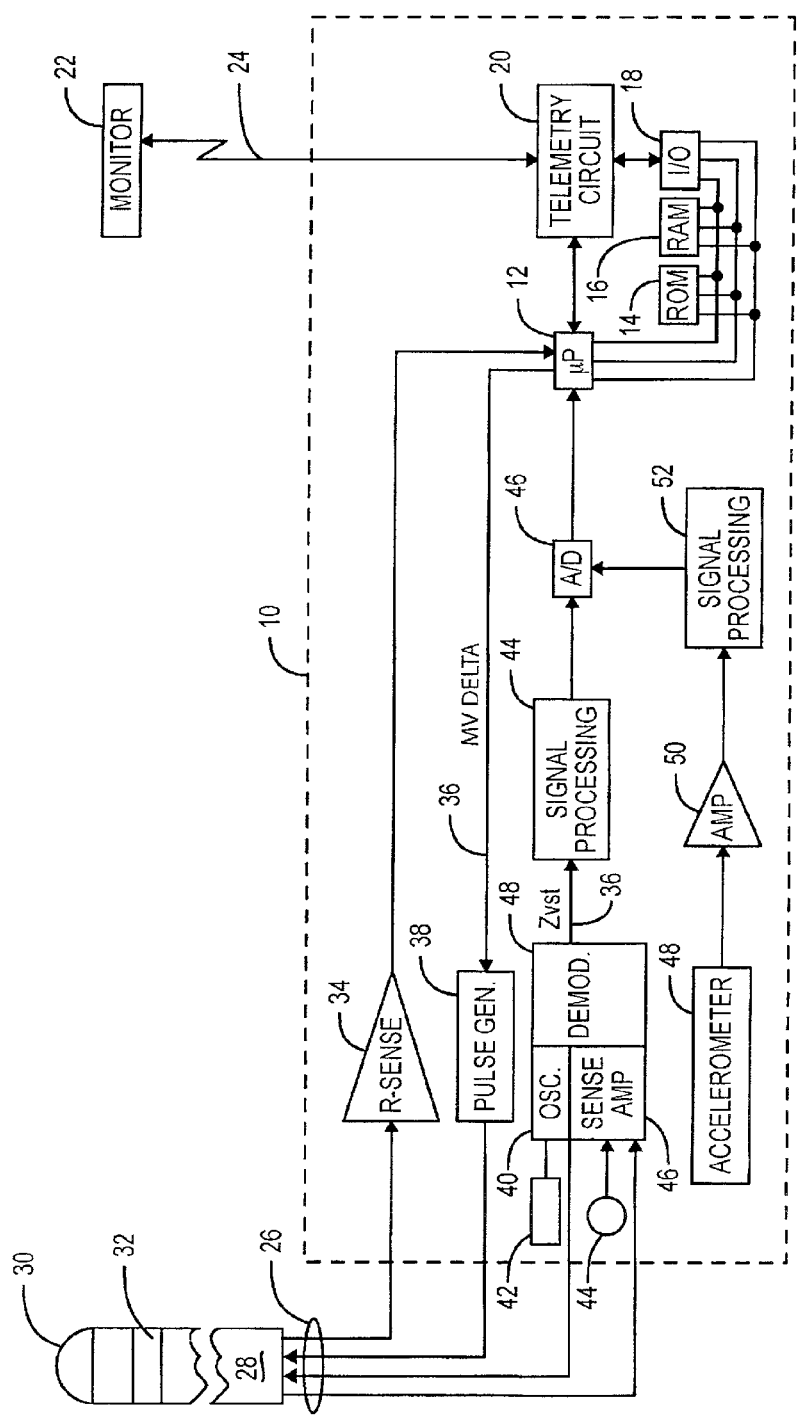
FIG. 1 is a block diagram of an implantable CRMD incorporating circuitry for capturing phonocardiograms and polysomnograms for subsequent readout to an external monitor.

With reference to FIG. 1, an implantable cardiac rhythm management device (CRMD) is shown as being enclosed in a broken line box 10 and, for exemplary purposes only, is represented as a rate adaptive pacemaker in which minute ventilation is the rate controlling parameter. As mentioned above, the implanted device may be purely diagnostic in nature and need not have a tissue stimulating capability.

The device includes a microprocessor 12 having a ROM memory 14 adapted to store a program of instructions, a RAM memory 16 for storing operands and data and an I/O module 18 for controlling a telemetry circuit 20 whereby bi-directional communications can be established between the implanted module 10 and an external monitor 22 via telemetry link 24. The implanted device 10 is connected to a cardiac site by conductors 26 in a pacing/sensing lead 28 having tissue contacting electrodes 30 and 32 thereon. Those skilled in the art will appreciate that one or more conductors 26 in the lead 28 may be eliminated with the remaining conductors shared between the sense and pace functions. Cardiac depolarization signals, e.g., R-Waves picked up by the electrodes 30 and 32, are applied by way of a sense amplifier 34 to an input of the microprocessor 12. Those skilled in the art can also appreciate that the implanted CRMD 10 may also include an atrial sense amplifier adapted to receive atrial depolarization signals (P-Waves) so that both P-Wave events and R-Wave events can be conveyed to the microprocessor 12.

Operating under control of a program stored in the ROM 14, the microprocessor 12 is shown in the exemplary embodiment as being connected in controlling relationship, via line 36, to a pulse generator 38 which is adapted to deliver tissue stimulating pulses, via the lead 28, to target tissue in the heart.

Being a rate adaptive pacemaker, means are provided for adjusting the rate at which the pulse generator 38 delivers its stimulating pulses to the lead 28. In the embodiment of FIG. 1, minute ventilation (MV) is provided as the rate controlling parameter. As such, an oscillator 40 is provided for delivering sub-threshold RF pulses, typically at a frequency of about 30 KHz, between an electrode 42, which may be located on the lead 28, and an electrode 44, which may be the metal can comprising the housing for the CRMD 10. As is well known in the art, respiratory activity (inhalation and exhalation) modulates the 30 KHz carrier signal, which is fed through a sensing amplifier 46 to a demodulator circuit 48. The demodulator functions to recover the modulating envelope. Changes over time in the trans-thoracic impedance caused by respiratory activity produces an analog signal on line 42 which is then fed through a signal processing circuit 44 and an analog to digital converter 46 before being applied as an input to the microprocessor 12. Those skilled in the art will appreciate that the A/D converter 46 may itself be implemented in the microprocessor 12 and need not necessarily be a separate module as depicted in FIG. 1.

In accordance with the present invention, there is also provided an accelerometer type transducer 48 within the CRMD 10 and its output is amplified at 50 and appropriately signal processed at 52 to remove DC baseline shift and signal energy due to body motion before being digitized by the A/D converter 46 and fed to the microprocessor 12.

Figure 2:
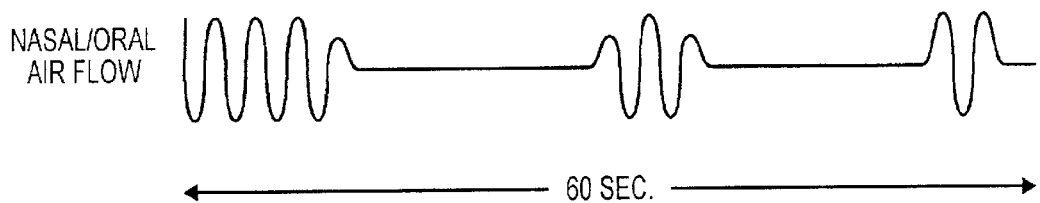
FIG. 2 represents a polysomnogram recording.

FIG. 2 illustrates diagrammatically a polysomnogram illustrating nasal/oral airflow evidencing apnea episodes. As mentioned above, Cheyne-Stokes respiration frequently appears in patients whose cardiac output is low due to CHF.

Figure 3:
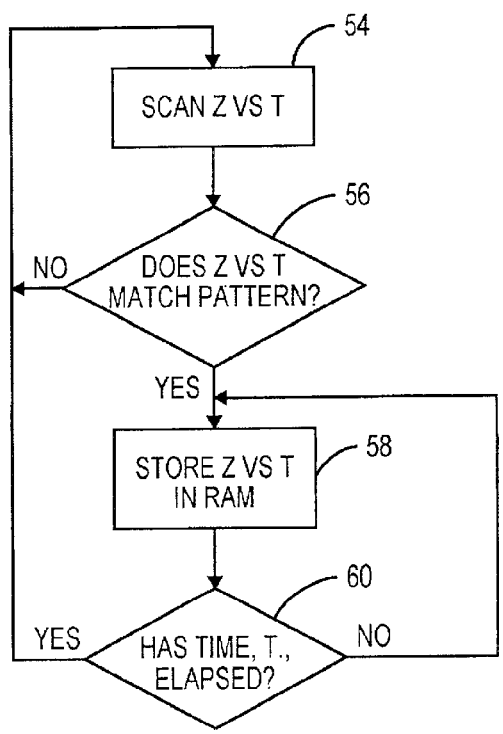
FIG. 3 is a software flow diagram of an algorithm for storing polysomnogram data.
Figure 4A:
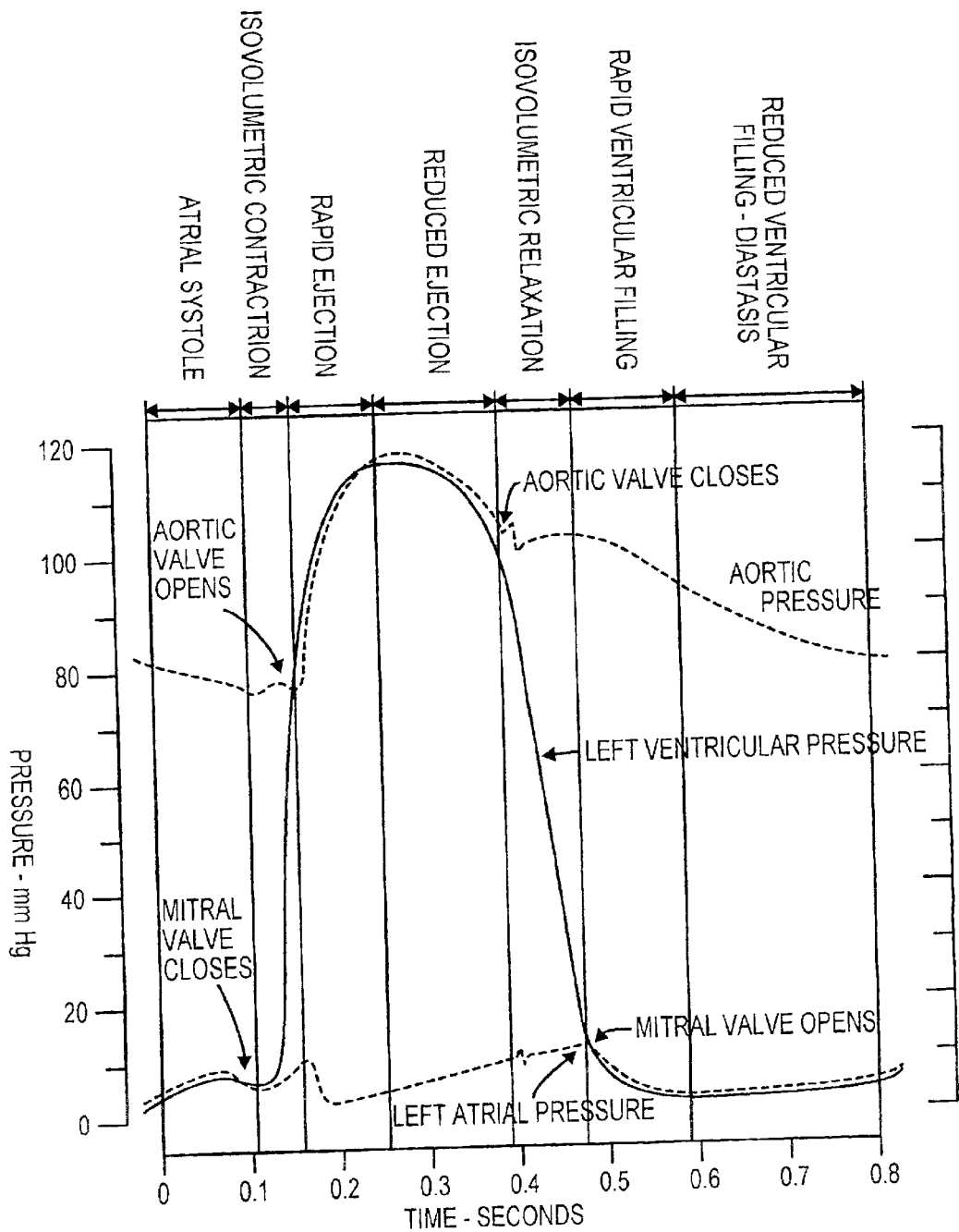
FIGS. 4A through 4D, when arranged as in FIG. 4, is a plot of left atrial, aortic, and left ventricular pressure pulses correlated in time with aortic flow, ventricular volume, heart sounds, venus pulse, and electrocardiogram for a complete cardiac cycle.
Figure 4B:
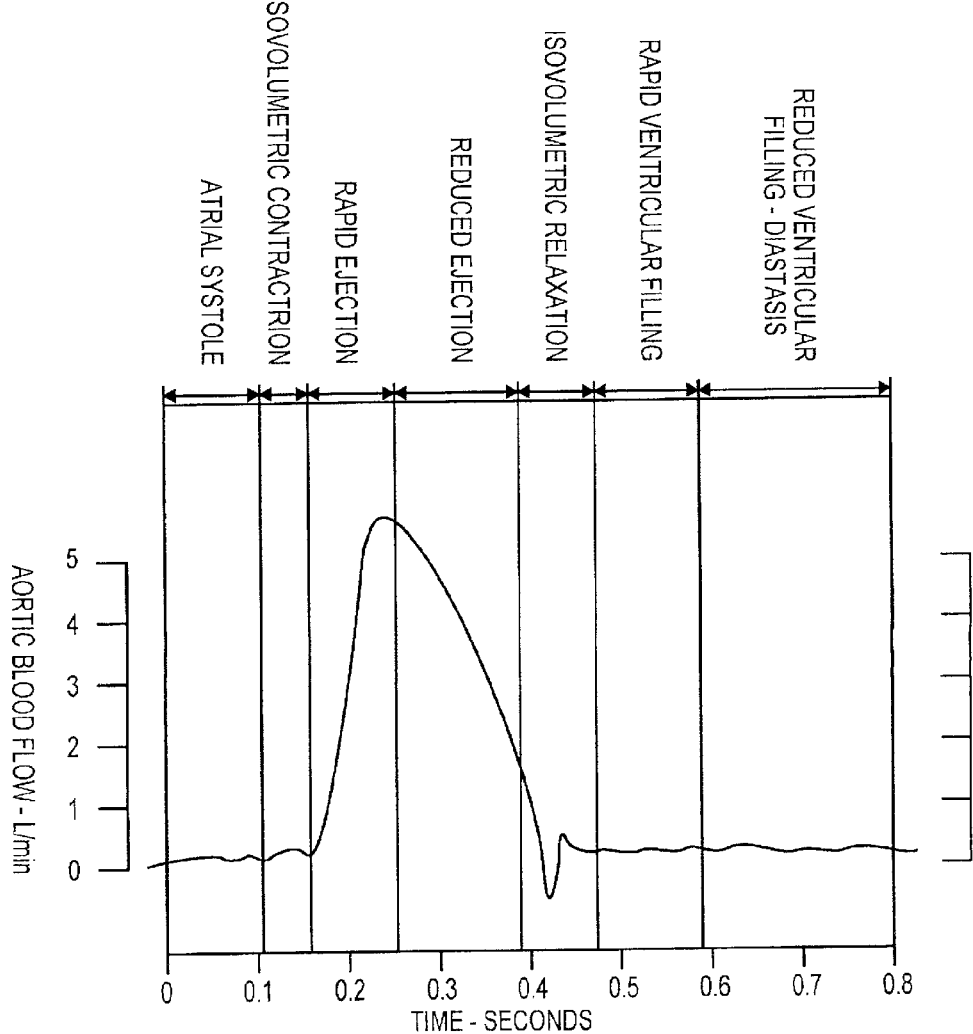
Figure 4C:
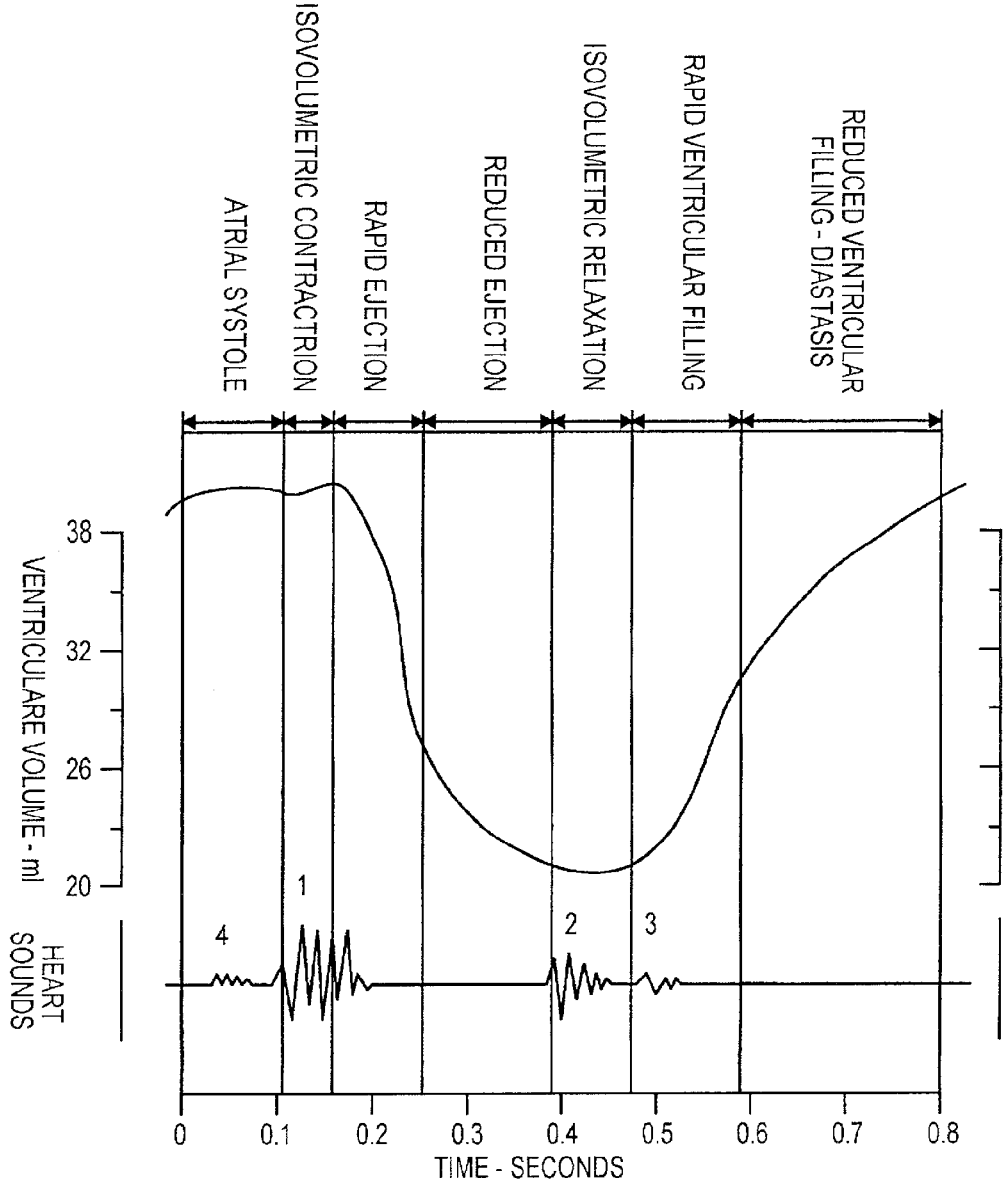
Figure 4D:
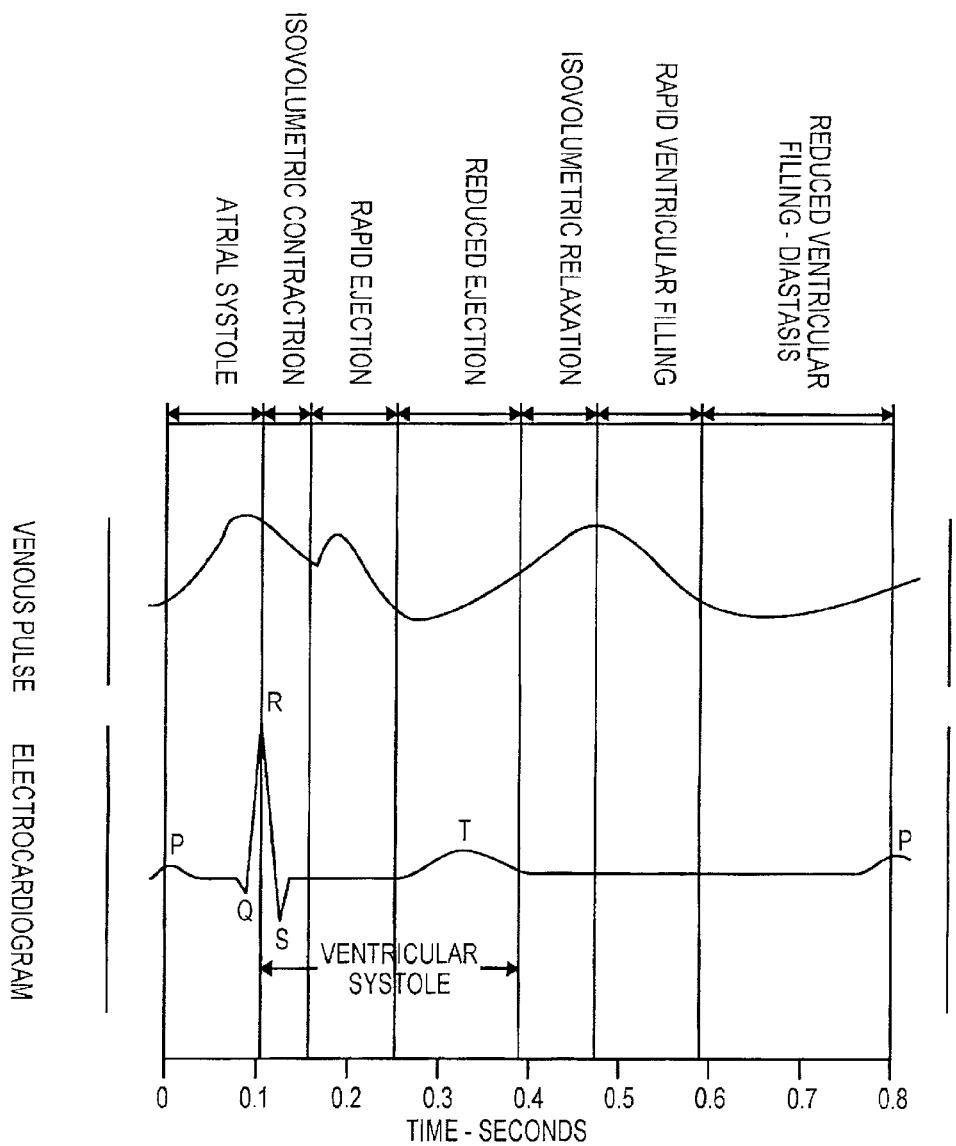

FIG. 3 is a simplified software flow diagram of an algorithm for triggering the capture (recording) of respiratory pattern information in the event that an abnormal pattern in terms of respiratory rate and/or tidal volume is sensed. At block 54 the microprocessor continues to scan the digitized output from the signal processing circuit 44 to determine whether the trans-thoracic impedance versus time output from the demodulator 48 matches a pre-determined pattern (Block 56). If a match is detected, the RAM memory 16 is enabled and the digitized polysomnogram information is stored therein (Block 58). The RAM continues to store the polysomnogram data until such time as the test at block 60 determines that a preprogrammed time interval sufficient to capture relevant respiratory data has elapsed.

Once the polysomnogram information is stored in the RAM, it can be later transferred, via I/O module 18 and the telemetry circuit 20, to an external monitor 22 for print out or display to a medical professional.

Referring next to FIG. 4, the correlation between heart sounds and events in the cardiac cycle is displayed for a patient with a normal heart. Also shown in the diagram of FIG. 4 are plots of left atrial, aortic and left ventricular pressure pulses that are correlated time wise with aortic blood flow, variations in ventricular volume, venus pulse and an electrocardiogram for one cardiac cycle.

Figure 5:
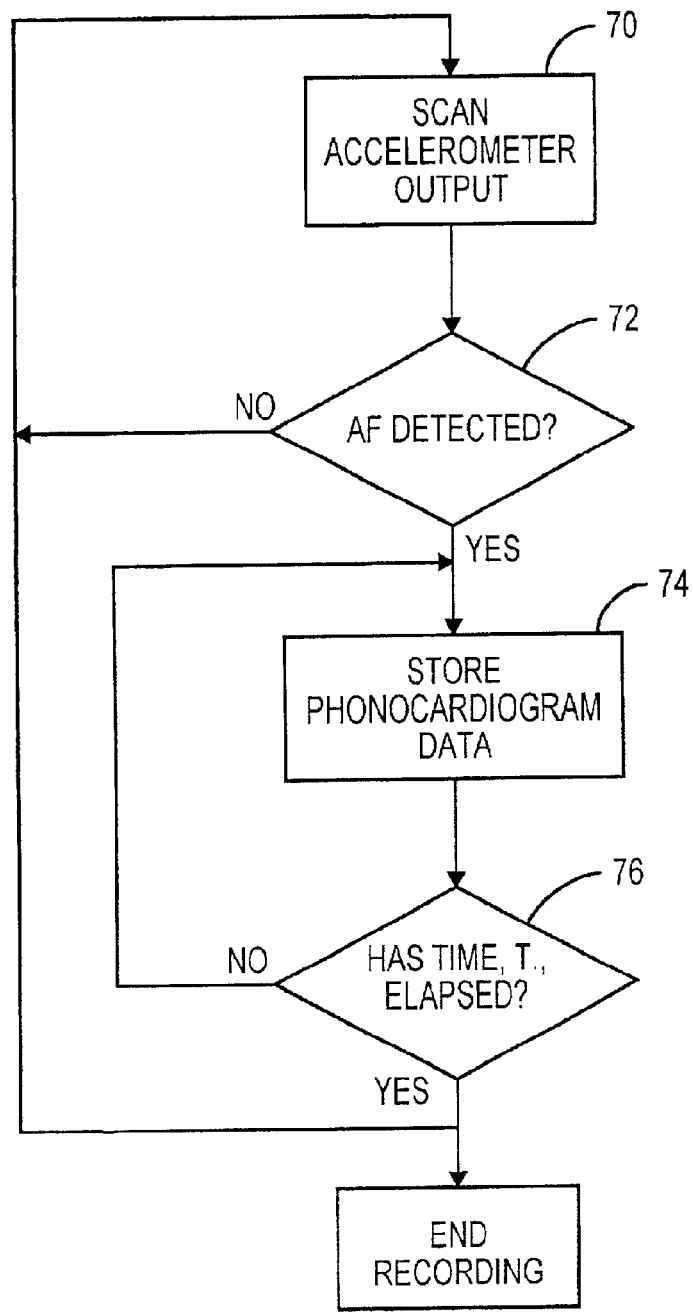
FIG. 5 is a software flow diagram of an algorithm for storing heart sound data.

FIG. 5 is a software flow diagram for triggering the recording of phonocardiogram data in the random access memory 16 in the CRMD 10 upon the occurrence of a pre-determined event. As indicated at block 70, the output from the accelerometer 48 is continually scanned by the microprocessor 12 and when a triggering event, such as the detection of atrial fibrillation (block 72), the RAM 16 is enabled to store the phonocardiogram data (blocks 74). The phonocardiogram data is recorded for a preprogrammed time interval, and when the programmed time interval times out (block 76) storage of the data in the memory terminates with control returning to the input of block 70.

A physician may select to record heart sounds based on criteria other than an episode of atrial fibrillation. For example, the test at block 72 may be based upon the patient reaching a certain level of exercise as determined by measured heart rate. Any other meaningful criteria may also be used as the triggering event for storing the phonocardiogram data.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the preferred embodiment cardiac rhythm management device has been described for use in a rate adaptive pacemaker, however, it may be used in a defibrillator, an antitachy pacer, a diagnostic-only device or in another type of implantable electronic device where it is desired to monitor polysomnograms and/or phonocardiogram data.

What is claimed is:

1. An implantable medical device comprising:
   a) a microprocessor-based controller;
   b) a memory controlled by the microprocessor-based controller;
   c) means for sensing variations in transthoracic impedance due to respiratory related activity; and
   d) means responsive to detection of a predetermined respiratory pattern for storing data pertaining to the sensed respiratory related activity in the memory.

2. The implantable medical device of claim 1 and further including a telemetry link in the device for transferring out the stored data to an external monitor.

3. The implantable medical device of claim 1 wherein the predetermined respiratory pattern is Cheyne-Stokes respiration.

4. The implantable medical device of claim 1 wherein the predetermined respiratory pattern is apnea.

5. A method of storing polysomnograph data in a memory of an implantable medical device comprising the steps of:
   a) implanting in a patient a medical device having a controller with a memory for storing data and at least one sensor for detecting variations in transthoracic impedance relating to respiratory activity and producing an electrical signal proportional to said variations;
   b) detecting a predetermined event; and
   c) storing polysomnograph data derived from the detected respiratory activity in the memory upon detection of said predetermined event.

6. The method of claim 5 wherein the predetermined event triggering storage of polysomnograph data is detection of a predetermined respiratory pattern.

* * * * *